Figure 1:
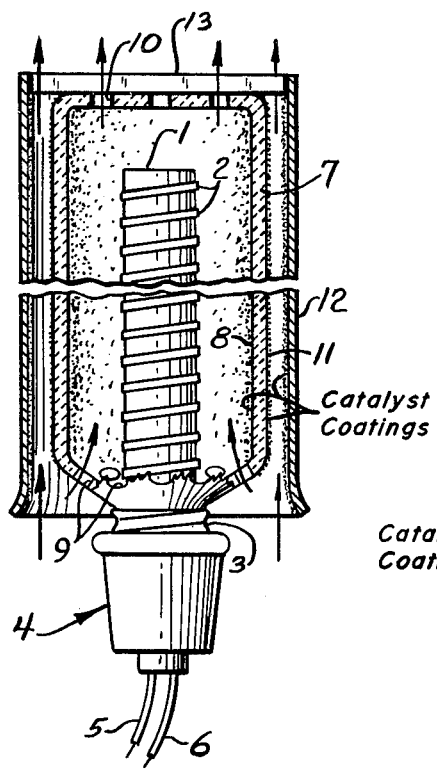

United States Patent [19]

Haensel

[11] 4,023,928
[45] May 17, 1977

[54] CATALYTIC FUME CONTROL DEVICE

[75] Inventor: Vladimir Haensel, Hinsdale, Ill.

[73] Assignee: UOP Inc., Des Plaines, Ill.

[22] Filed: Sept. 19, 1975

[21] Appl. No.: 614,809

Related U.S. Application Data

[63] Continuation-in-part of Ser. No. 396,949, Sept. 13, 1973, abandoned.

[52] U.S. Cl. .................................. 21/74 R; 21/119; 21/120; 21/122; 23/288 FC; 219/374; 219/381

[51] Int. Cl.$^2$ .................... A61L 9/00; B01J 35/04; F24H 3/00

[58] Field of Search .......... 219/356, 357, 374, 381; 23/288 F, 288 FL, 288 E, 288 J; 21/120, 74, 53, 122, 119

[56] References Cited

UNITED STATES PATENTS

| | | | |
|---|---|---|---|
| 1,678,778 | 7/1928 | Harter | 23/288 E X |
| 1,901,038 | 3/1933 | Marshall | 219/374 X |
| 2,668,993 | 2/1954 | Bair | 21/120 |
| 3,001,295 | 9/1961 | Miller | 23/288 FC |
| 3,395,972 | 8/1968 | Hardison | 23/288 F |
| 3,443,911 | 5/1969 | Keith et al. | 23/288 F |
| 3,768,982 | 10/1973 | Kitzner et al. | 23/288 FC |
| 3,923,458 | 12/1975 | Moran | 21/120 X |

Primary Examiner—Morris O. Wolk
Assistant Examiner—Michael S. Marcus
Attorney, Agent, or Firm—James R. Hoatson, Jr.; Philip T. Liggett; William H. Page, II

[57] ABSTRACT

An electric lamp bulb or electric resistance coil is provided to radiate heat to one or more adjacent surfaces which have an active oxidation catalyst such that fumes and odors in the confines of a room that are drawn over the catalytic surface will be converted to less objectionable products. A catalytic device with an incandescent light bulb type of heating element is of particular advantage in that it can readily be screwed into a lamp base or mounted in other forms of current supplying receptacles and, in addition to a light source, will provide a heat emitting surface for heating the catalyst surface and inducing natural air convection current flow past the catalytic surface. Also, a fume control device which utilizes a resistance heating coil can readily provide both radiant heat and convection heat so that there will be the dual function of fume oxidation from air flow past a heated catalyst surface and radiant heat into a room area. Various types of catalyst coatings and/or catalytic wrappings may be used on the refractory surfaces which will be radiantly heated by the manually mountable-demountable form of bulb or resistance heating element.

1 Claim, 6 Drawing Figures

CATALYTIC FUME CONTROL DEVICE

CROSS-REFERENCE TO RELATED APPLICATIONS

This application is a continuation-in-part of my co-pending application Ser. No. 396,949, filed Sept. 13, 1973 and now abandoned.

The present invention provides a small, portable form of catalytic fume control device which is particularly adapted for manual placement in a room or other relatively small confined zone. More particularly, there is provided a refractory surface with a coating of active oxidation catalyst at a spaced distance from a heat producing light bulb or suitable electrical resistance element with a threaded or plug-in lower portion, such that the resulting device can be of the nature of small lamp or small room heater.

Most catalytic converters used in industrial installations for converting oxidizable noxious fumes, or used for effecting the conversion of automobile exhaust gases, prefer relatively high temperature levels of the order of 600° F. or more to provide for rapid fume ignition and good conversion efficiencies, although it is realized that with an extended period of time, even at conventional room temperature conditions, there can be catalytically promoted oxidation reactions and conversions. For example, in connection with large commercial processing units, or with drying oven fumes, etc., where objectionable gases and vapors are being released, it is customary to heat the gaseous stream to at least the 600° to 700° F. level prior to passing such fumes through catalytic mats such as taught and described in U.S. Pat. Nos. 2,720,494 and 2,658,742. Also in connection with auto exhaust gas converters, it has been deemed desirable to position the catalytic type of reactors closely adjacent the exhaust gas manifolds such that the high temperature of the exhaust gas stream itself will improve the ignition and overall efficiency of the catalytic conversions taking place. However, in considering the various aspects of providing a portable catalytic converter device which may be used in a room, or other generally small zone, it was realized that it could be impracticable to try and heat the air in the room to any 600° to 700° F. level and that it was preferable to heat a catalytic surface so as to at least enhance the catalytic conversion of smoke, cooking odors, and other objectionable fumes which may enter a living area, particularly in comparison with the rate of reaction which would take place at ambient, room temperature, conditions.

It is thus a principal object of the present invention to utilize a light bulb or other conveniently mountable heating element for supplying heat to a catalyst surface on a refractory support which, preferably, will be supported from the heating element or from the same base as is used for the electric power supply socket means, such that a readily connectable and portable type of device is provided.

It may be considered a further object of the present invention to provide a combination lamp-converter with not only the convenience, utility and portability of a lamp, but, additionally, a catalytic device which will utilize the heat output of a bulb type of resistance heating element to cause natural convection current air flow to pass over the catalytic surface(s).

In another aspect, it may also be considered an object of the invention to provide a combination heater-fume incinerator in that the heating element can be used to not only heat the spaced apart catalyst surface but, additionally, can provide radiant and/or convected heat into a room.

In one embodiment, the present invention provides a catalytic converter for use in purifying the air in a room or generally small zone, which comprises in combination, a central electrical resistance heat source, at least one refractory wall member spaced from said heat source to receive radiant heat therefrom and form at least one vertically oriented air passageway means therebetween, and an active catalytic covering on said refractory wall member to provide for catalytic conversion of combustible components in the air stream which will be drawn through said passageway means and caused to flow over catalyst on the wall member.

In a further embodiment, and as heretofore noted, the heating element to provide the radiant heat to the catalytic surface may comprise a conventional high wattage electric light bulb; however, it is not intended to limit the present invention to any one type of central heating element inasmuch as a resistance coil means may well be used. The wire of the coil can be wrapped around a central porcelain core member, such as used in small electric space heaters, or it may be held by mica or other heat resistance support material, such as used in electric toasters and the like.

Where the light bulb or coil is placed centrally in an encompassing, but spaced apart, catalytically coated wall member, there can be not only fume oxidation but room lighting to the extent that light beams can be directed upwardly, and downwardly, from the open-ended air passageway space. In addition, there can be room heating from the convection current action of room air and by heat radiation from the heated encompassing wall member. Heat output can be regulated by the choice of wattage for the heating source and the overall size of the device. A high heat output element can serve to heat a large catalytically coated or covered wall member while a low output element will necessitate a more closely spaced wall member as well as less surface area to insure its receiving adequate surface heating.

In addition, there can also be combination converter-heater devices where the heat producing bulb or coil is not entirely encompassed by the catalytically coated wall member so that radiant heat and light can advantageously be projected and radiated outwardly into a room as well as against an opposing, spaced apart catalytically coated wall member. There will, of course, still be provided in all embodiments a space for generally vertical air flow between the heat source and the coated surface to effect the desired continuous convection current flow in the room and the catalytic conversion of entrained fumes.

Preferably, in each instance, the heating element will have a screw-in type of base or projecting prongs such that there may be easy and fast mounting of the heating element into a conventional form of electric socket or receptacle. It is, of course, possible to use other than the threaded base and socket arrangement. For example, there may be a construction where there is a plug-in and quarter-turn insertion such as used with auto lamp bulbs or, optionally, there could be a current supplying mounting with means to receive prongs such as conventionally used with radio tubes and the like.

The spaced refractory wall to hold the catalytic surface may be coated or otherwise covered on only the portion of the wall member which faces the central heating element or, preferably, such wall member will be coated on both sides such that air and fumes which pass over the entire wall surface will be oxidized and purified. The refractory wall itself may comprise metal, porcelain, ceramic, or other refractory inorganic base material suitable for supporting catalyst coatings. Where the wall member is formed of metal it will necessarily have its surface prepared so as to have porosity and retain an active catalytic coating. For example, base materials of metal may be coated in manner set forth in U.S. Pat. No. 3,492,148, wherein there is taught the method of placing a porcelain coating over the metal and a subsequent layer of porous alumina in turn providing a desirable porous surface for an active oxidation catalyst. The preferred form of catalyst supporting wall member may comprise a ceramic type of refractory material such as mullite, cordierite, spodumene, petalite, sillimanite, alumino-silicates, etc., all of which have somewhat greater porosity than typical porcelain materials although a porcelain type of material may well be utilized in the present invention. In addition, there may be a highly porous alumina coating over the ceramic material.

It is to be futher noted that it is not intended to limit the present catalytic device to the use of any one type of oxidaton catalyst coating to be used on the spaced wall member and such coating may include the metals of Groups I, V, VI and VIII of the Periodic Table, particularly, copper, silver, vanadium, chromium, iron, cobalt, nickel, platinum, palladium, with a component being used singly or in combinaton with one or more other active components. Of course, for the conversion of fumes and noxious components in a room at ambient conditions, it is preferable to use a highly active noble metal component such that there is more efficient conversion of oxidizable components at the low temperature conditions. The active component(s) may be composited with, or supported by, a suitable refractory inorganic oxide, such as alumina or alumina combined with one or more other refractory inorganic oxides. As heretofore set forth, the oxide supporting layer can be applied to the wall surface prior to the coating of an active catalytic component although there may be a mixture made of the refractory metal oxide support material with the active component and the mixture sprayed, dipped, or otherwise coated onto the wall surface. Additionally, reference may be made to U.S. Pat. No. 3,565,830 which sets forth various methods for coating a refractory support member with an alumina slip and an active catalytic coating.

Although it is generally preferred that the spaced refractory wall member for the present invention will be suitably coated with a tenacious active oxidation catalyst material, there may be the covering of at least a portion of the spaced wall member with a catalytically impregnated temperature resistant gauze or mesh, such as may be formed from asbestos, mineral wool, fiber glass, alumina fibers etc., with the porous fibers being in turn impregnated or otherwise coated with an active oxidizing catalyst material.

In order to provide portability and ease in utilization of the present improved form of catalytic device, it is also a feature of such device to have means for readily mounting or removing the catalytically coated refractory wall member from around the centrally located lamp bulb or heating element. For example, the spaced catalytically coated refractory wall member may be hung or otherwise supported from the top of the heating element such that the entire unit is, in effect, supported from the bulb or heating element that is mounted in the electric current supply socket means. In an alternative manner, the wall member may be supported from a lower portion of the heating element; however, the support means should be constructed and arranged to allow for convection current flow upwardly along the inside wall surface of the refractory catalyst support member in an annular-form flow stream. In still another arrangement, there may be the support of the catalyst covered wall member from the lamp base or from the electrical socket or receptacle means rather than from the heaing element itself. However, again, in all instances, there will be provision to permit convection flow to pass upwardly through the space being provided between the external portion of the central heating element and the inside wall of the catalyst supporting member. In still further alternative arrangements, there may be the utilization of more than one spaced refractory wall member such that a plurality of convection flow streams are created around the device and, where desired, there may be additional catalyst coatings provided on the additional wall member(s) to provide still further catalyst surface area for the particular device.

Reference to the accompanying drawing and the following description thereof will serve to illustrate variations in the types of central heating elements and variations in the means for forming, spacing and supporting the radiantly heated catalyst coated refractory wall members such that there may be the additional functions of heating and lighting, as well as point out advantages obtained from proper placement of the various portions of the device to enhance convection air stream flow.

FIG. 1 of the drawing is an elevational view, partially in section, which indicates that both internal and external catalytic surfaces may be used on one or more spaced refractory wall members and heat provided from a centrally positioned electrical resistance coil.

Figure 2:
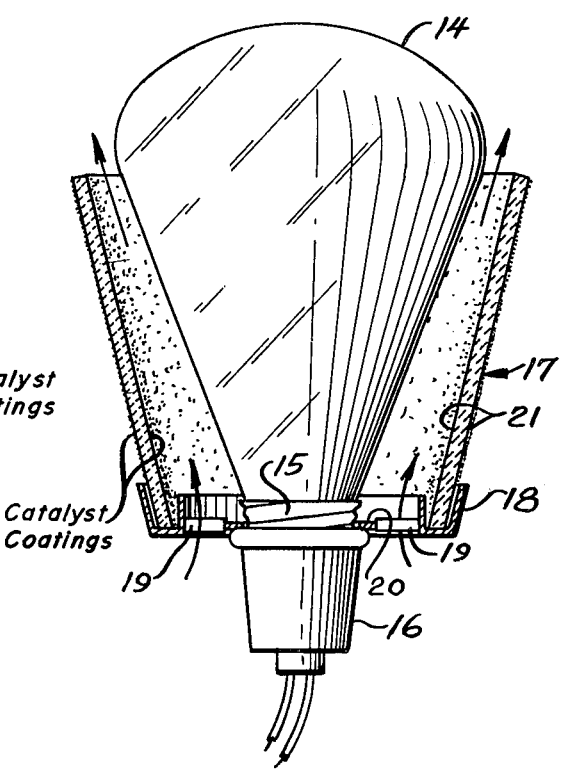

FIG. 2 of the drawing indicates diagrammatically, and partially, in section, a simplified form of device using an electric lamp bulb type of central heating element in combination with a frustra-conical form of catalytically coated wall member.

Figure 3:
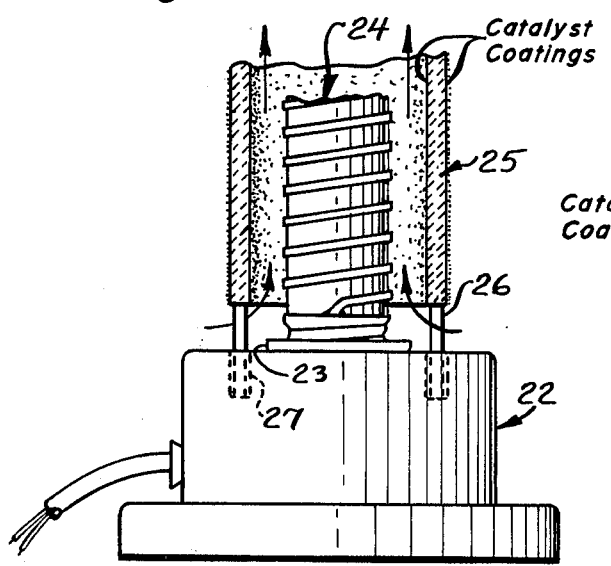
Figure 4:
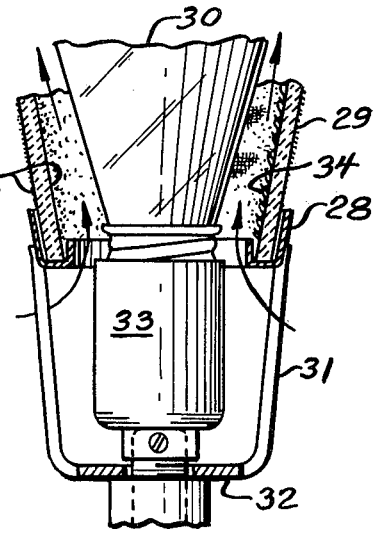

FIGS. 3 and 4 of the drawing indicate in partial sectional elevational views variations in supporting the catalyst coated wall member around a centrally positioned heat supplying element.

Figure 5:
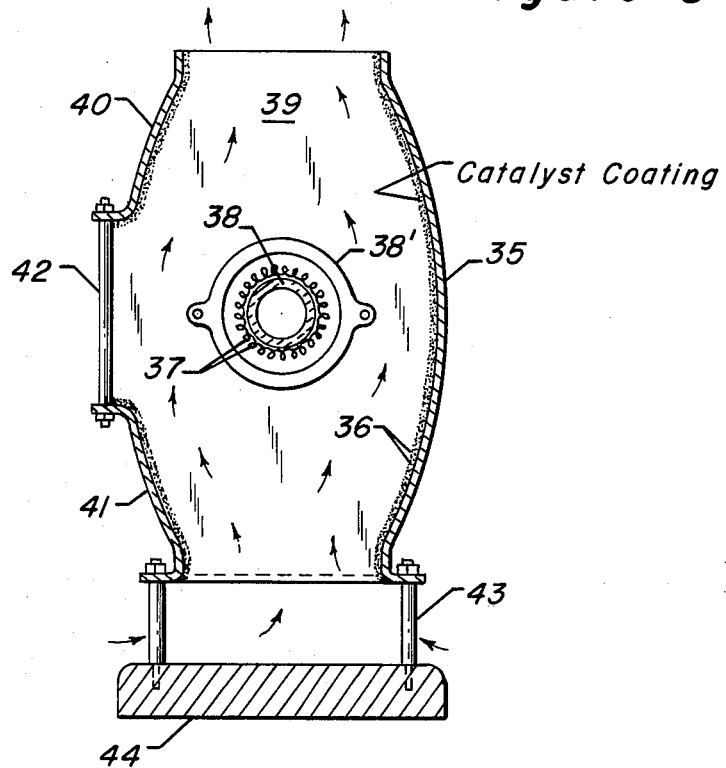
Figure 6:
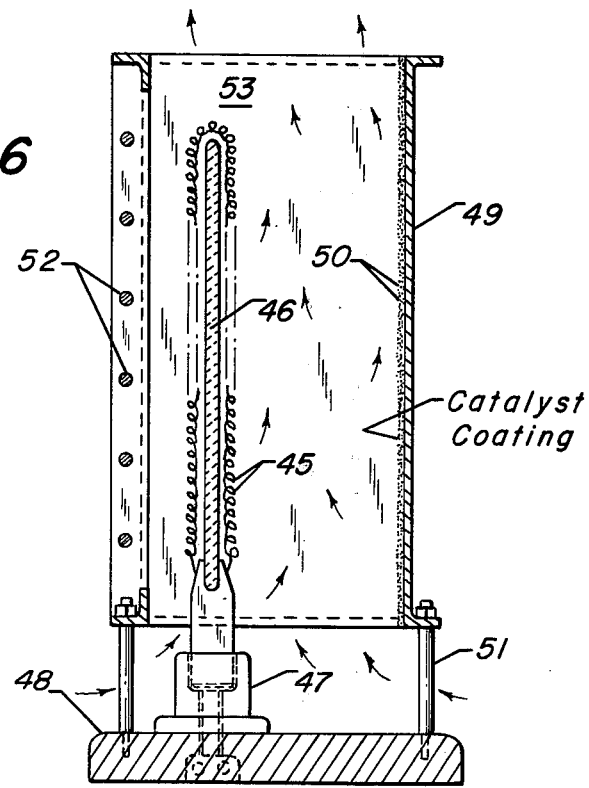

FIGS. 5 and 6 are diagrammatic sectional elevational views of embodiments which illustrate combination heater-catalytic fume converters capable of providing both radiant heat and convection current air flow.

Referring now particularly to FIG. 1 of the drawing, there is indicated a central refractory member 1 for supporting electrical resistance coil 2 which connects through a lower base portion to a threaded base member 3 which in turn is adapted to be screwed into an electrical socket 4 that receives electric current by way of lines 5 and 6. Extending around and also supported by the metal base 3, there is provided a catalytically coated cylindrical form refractory wall member 7 which has a catalyst coat 8 on at least the inside wall thereof to receive the high temperature radiant heat from coil 2.

In order that there will be enhanced convection flow through and around the present form of catalytic device, there are indicated a plurality of openings such as 9 in the lower portion of wall member 7 and openings 10 in the upper portion thereof, or optionally, there may be an entirely open upper end whereby air flow will pass upwardly in an annular-form flow stream along the interior catalyst coating 8. A preferred construction may also provide a catalyst coating 11 on the exterior wall surface of the refractory wall member 7 such that the air flow upwardly and therearound will also provide for catalytic oxidation of entrained fumes.

As still another embodiment, there may be an additional wall member, such as cylinder 12, which will be supported at a spaced distance from the exterior surface of 7 whereby still another annular-form convection stream will be caused to pass over the exterior catalyst surface 11. This exterior wall surface 11 will also be at a relatively high temperature by virtue of the heat being transferred by conduction through the wall member 7. In addition, there may be catalytic coatings on the wall member 12 to still further provide greater catalyst surface area for the unit; however, catalytic conversion will obviously be carried out at a reduced rate, by virtue of the lower temperature contacting, on the wall member 12. In the embodiment of FIG. 1, there is indicated the use of spaced bar means 13 which will extend transversely across the upper portion of the cylindrical form wall member 12 and in turn provide support from the upper end portion of refractory wall 7; however, other forms of wall supporting means may well be used for this external member 12.

In FIG. 2 of the drawing, there is indicated a combination lamp-catalytic converter type of unit where a lamp bulb type of member 14 with a threaded, screw-in, type of base 15 for mounting in electrical socket means 16, will provide the source of radiant heat to a spaced catalytically coated refractory wall member 17. The latter is indicated as being supported from a suitable ring-form trough 18 that is held by arm members 19 to a ring member 20, which, is turn, rests on the upper portion of socket means 16. By the use of spaced arm members 19, there is permitted air flow upwardly around the outside of the high wattage lamp bulb 14 and along the interior surface of wall member 17 in order to enhance natural convection air flow upwardly through the device. In accordance with the present invention, the refractory wall member 17 will be provided with an active catalyst coating 21 on at least the interior surface thereof where there is a relatively high temperature available for the catalyst to effect the conversion of oxidizable materials being carried in the air stream passing over the wall member 17. Inasmuch as the outer wall surface of 17 will also have a relatively high temperature, it is preferable that the exterior surface thereof will also have a catalyst coating in order to provide additional active surface for contacting the air flow which passes therearound. Although not shown in the drawing, an additional coated or uncoated refractory wall member may be supported at a spaced distance from the exterior wall of member 17 (such as wall 12 in FIG. 1) in order to enhance convection flow and provide additional surface for catalyst coatings.

In FIG. 3 of the drawing, there is indicated the use of a large base member 22, of the nature of lamp base, with a suitable electric current supplying socket means 23 to hold a central heating element 24 as well as support a spaced catalytically coated refractory wall member 25. The latter is indicated to be of cylindrical shape spaced from the heating element 24 and supported on spaced leg members 26 that are adapted to fit into recess means 27 in base member 22. The spaced apart leg members 26 are utilized such that there may be an air stream opening to permit convection flow upwardly along the inside catalyst coated surface of wall member 25, with heating element 24 creating a chimney effect to enhance the convection flow. Additionally, there may be a catalyst coating on the exterior wall of refractory member 25 so as to permit conversion of entrained odors that pass along the outside of the wall.

In still another arrangement, such as shown in FIG. 4, there is the use of a channel member 28 to support a cylindrical or conical-form refractory member 29 around a lamp bulb type of heating element 30 and spaced rod-like leg members 31 are connective wth a ring member 32 to effect the support of channel member 28. In this modification, the spaced catalyst coated wall member 29 is supported from its lower periphery by a support means that extends from below a socket means 33 which is part of a lamp base or other form of socket supporting means. As will be obvious from FIGS. 3 and 4 of the drawing, still other support means may well be utilized within the scope of the present invention to effect the support of the centrally positioned heating element as well as hold the spaced catalytically coated refractory wall member which is provided to encompass the heating element at a spaced distance. However, in all instances, there shall be support means which will permit air flow to reach the annular space between the heating element and the inside surface of the wall member such that there is a chimney-effect air flow over the catalyst surface. Although not shown in either of the embodiments of FIGS. 3 and 4, there may be additional spaced baffle members around the respective refractory wall members 25 and 29 so as to provide additional convection current flow zones and still further catalyst surface area to contact the entrained odors in the air flow streams which will come in contact with the catalytic device.

It is not intended to limit the present invention to any one type of bulb or heating element and still other variations may be utilized than those shown and described and there may be variations in electrical wattage consumed and temperature levels radiated to the catalytically coated wall members. Even with the use of 110–115 volt electrical supply, there may be wattage outputs of the order of 1000 to 1400 watts and resulting temperature levels of the order of 500°–600° F. on the inside surface of spaced refractory members so as to provide good catalytic conversion of such fumes as may pass over the surfaces. However, lower wattage and less radiant heat may well be utilized to permit somewhat slower rates of catalytic conversion that will still provide substantial improvement as compared with unheated ambient conversion conditions. For light producing purpose, the heat elements of the apparatus embodiments of FIGS. 1 and 3 can be made to provide varying glow intensities from dull red to bright red, and thus serve the dual purposes of being a lamp and a fume incinerating device. Also, these same embodiments may use a high wattage incandescent lamp bulb to provide reading light intensities and high heat output.

In lieu of a dipped or applied catalytic coating to the surface(s) of the encompassing wall member of the device, there may be a catalytically active temperature resistant covering material, such as 34 shown on a part of the inside wall of 29 in FIG. 4. Such covering may be sized to fit over or onto the wall surface, or may be held by a suitable adhesive, or whatever, to provide a desirable oxidizing catalyst surface. A catalytic covering material may also be utilized on the exterior of the refractory wall member(s) of any of the various shapes and emobdiments used with a particular device.

FIG. 5 of the drawing shows a generally rectangular form of combination radiant heater and fume converter where at least a rear wall portion 35 is catalytically coated on the surface 36 facing the heater coil 37. In this instance the latter is indicated as being supported on a refractory tubular member 38 that screws or plugs into a suitable electrical current supplying socket means 38' which is, in turn, mounted on an end wall member 39. There is also indicated a "front" wall portion that has upper ad lower coated sections 40 and 41, as well as a central open section with a protecting screen or spaced bars, such as 42, which will permit some of the radiant heat from coil 37 to be directed laterally into a room or other confined spaced to be heated. The lower ends of the elongated wall portions 35 and 41 are shown as having flanged portions which can provide means for effecting their support from spaced pins or leg members 43 that, in turn, extend from a suitable base member 44. As a result, there is a suitable elevated support of the wall members to permit convection current flow of air from the room, as shown by the arrows, to carry any undesired fumes in the air past the heat source and over the catalytically coated surfaces.

In a sightly modified form of combination heater and fume converter, the device shown in FIG. 6 provides an electrical resistance coil 45 on a rectangular form of refractory support member 46 that may be plugged into and supported from a current supplying socket 47 on a base 48. This particular modification indicates a generally straight and vertical "rear" wall section 49 with a catalytic coating 50 that is spaced from the heat producing coil 45 in a manner to permit a convection current flow in the space therebetween, as also shown by the arrows. The wall 49, as well as end and front wall portions, will also be spaced from the base 48 by suitable leg means 51 to readily permit air flow into the lower end of the device and out the open top portion. The device of FIG. 6 varies from that of FIG. 5 in providing a greater open area at the "front" portion of the device by having only spaced bars or protecting grid means 52 extending between suitable end walls, such as 53. In other words, in this embodiment, the plate-like refractory support 46 for coil 45 will serve to define, along with rear wall 49, a flow path for convection air flow over the catalyst surface 50.

It will be obvious that still other arrangements can be provided to result in combination radiant heater means and convection heat flow so as to have the oxidation of fumes entrained with continuous convection air flow that will be set up within the device. Wall members can be of ceramic type refractories, or of metals, that will be coated or otherwise covered with a catalytic material in accordance with any of the procedures hereinbefore set forth.

I claim as my invention:

1. A portable catalytic converter device for use in purifying the air in a room or generally small zone, which comprises in combination, a central electrical resistance heat source having a terminal end portion for replacement mounting into an electric current supplying socket, a refractory wall member spaced from said heat source to receive unobstructed radiant heat from the heat source and form an open-ended vertically oriented air passageway therebetween thereby to permit convection flow therethrough, support means for said wall member retaining said wall member spaced from said heat source, an active catalytic covering on the surface of said wall member facing said heat source for catalytically converting combustible components in the air stream flowing through said passageway and over the catalytic coating on the wall member, and a base support means, said heat source and said refractory wall member being mounted upon said base support means.

* * * * *